United States Patent
Chahwala et al.

(10) Patent No.: US 6,887,886 B2
(45) Date of Patent: May 3, 2005

(54) THERAPEUTIC COMPOSITIONS COMPRISING EXCESS ENANTIOMER

(75) Inventors: Suresh Babubhai Chahwala, County of Kent (GB); Michael George Dodd, County of Kent (GB); Michael John Humphrey, County of Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/930,330

(22) Filed: Aug. 15, 2001

(65) Prior Publication Data

US 2002/0045648 A1 Apr. 18, 2002

Related U.S. Application Data

(60) Provisional application No. 60/237,168, filed on Oct. 2, 2000.

(30) Foreign Application Priority Data

Aug. 23, 2000 (GB) .............................................. 0020842

(51) Int. Cl.[7] ............................................ A61K 31/445
(52) U.S. Cl. ...................................................... 514/315
(58) Field of Search ........................................ 514/315

(56) References Cited

U.S. PATENT DOCUMENTS 5,438,145 A * 8/1995 Furlan et al. ................ 546/321
5,750,707 A * 5/1998 Spargo ........................ 546/321
6,046,338 A * 4/2000 Spargo ........................ 546/322
6,080,761 A * 6/2000 Chahwala et al. ........... 514/330
6,333,342 B1 * 12/2001 Foster ......................... 514/356

FOREIGN PATENT DOCUMENTS

EP 0754043 10/1994 .......... A61K/31/44

OTHER PUBLICATIONS

Budavari et al., The Merck Index, Twelfth Edition (1996), pp. 86 and 87, abstract no. 516.*
J. Med Chem 29 1696 (1986), Arrowsmith, et al.
J Med Chem 35 3341–3344 (1992), Goldmann et al.
Kidney International 49 S2–S5 (1996), Igarro.
Amer J. Cardiol 73 A10–A17 (1994), D. N. Abernethy et al.
Circ Res 86 270 (2000), H. Tada et al.
J. Cardiovasc Pharmacol 35 195–202 (2000), Zhang, et al.
Circulation 97 576 (1998), Zhang and Hintze.
Am J. Cardioll 83 92H (1999), Mital et al).
J. Cardiovasc Pharmacol, vol. 12 (Suppl. 6), 1988.

* cited by examiner

Primary Examiner—Kevin E. Weddington
(74) Attorney, Agent, or Firm—Scully, Scott, Murphy & Presser

(57) ABSTRACT

The present invention is concerned with pharmaceutical compositions comprising a mixture of amlodipine enantiomers, which compositions have both anti-hypertensive and additional cardiovascular properties derived respectively from their calcium channel-blocking activity and their ability to release vascular nitric oxide (NO).

19 Claims, No Drawings

THERAPEUTIC COMPOSITIONS COMPRISING EXCESS ENANTIOMER

CROSS-REFERENCE TO RELATED APPLICATIONS

The present application is a U.S. non-provisional application. This application claims the benefit of U.S. Ser. No. 60/237,168, filed on Oct. 2, 2000, under 35 USC 119(e).

FIELD OF THE INVENTION

The present invention is concerned with pharmaceutical compositions comprising a mixture of amlodipine enantiomers, which compositions have both anti-hypertensive and additional cardiovascular properties derived respectively from their calcium channel-blocking activity and their ability to release vascular nitric oxide (NO).

BACKGROUND OF THE INVENTION

Amlodipine is a well-known calcium channel-blocking agent which is used in the treatment of hypertension and angina. Amlodipine is a dihydropyridine with an asymmetric centre at the 4-position; presently, amlodipine is only approved for administration in the form of the racemate, specifically that of the besylate salt.

The individual enantiomers of amlodipine have been isolated (*J Med Chem* 29 1696 (1986), Arrowsmith et al) and identified as R(+) and S(−) (*J Med Chem* 35 3341–3344 (1992), Goldmann et al). The calcium channel-blocking activity of the racemate has been found to reside largely, but not exclusively, in the S(−) enantiomer (*J Cardiovasc Pharmacol* 12 (Supp 6) S144, J W Rigby et al).

European Patent No. 0754043 describes the surprising ability of the R(+) enantiomer of amlodipine to inhibit PDGF-induced vascular smooth muscle cell migration using an in vitro system which effect may prove to be useful in the treatment of conditions such as atherosclerosis, restenosis after angioplasty and endometriosis.

BRIEF SUMMARY OF THE INVENTION

In one aspect, the present invention relates to a pharmaceutical composition comprising an NO-releasing amount of the R(+) enantiomer of amlodipine or of a pharmaceutically acceptable salt thereof, an anti-hypertensive amount of the S(−) enantiomer of amlodipine or of a pharmaceutically acceptable salt thereof and a suitable excipient, diluent, or carrier, characterized in that said enantiomers are present in a ratio by weight (based on free base) of R(+) enantiomer:S(−) enantiomer of greater than 1:1.

In a further aspect, the present invention further relates to the use of the R(+) enantiomer of amlodipine or of a pharmaceutically acceptable salt thereof in the manufacture of a medicament for the treatment of a condition for which a vascular NO-releasing agent is indicated.

In an even further aspect, the present invention further relates to the use of the R(+) enantiomer of amlodipine or of a pharmaceutically acceptable salt thereof in the manufacture of a medicament for the treatment of a condition for which both an anti-hypertensive agent and a vascular NO-releasing agent are indicated.

DETAILED DESCRIPTION OF THE INVENTION

In the present invention, it has now been found that the R(+) enantiomer of amlodipine has another unexpected property, specifically the ability to release NO, a potent vasodilator and inhibitor of platelet aggregation and the active species in nitroglycerin (*Kidney International* 49 S2–S5 (1996), Ignarro), from endothelial and vascular smooth muscle cells (hereinafter referred to as "vascular NO").

When amlodipine is administered as the racemate, the NO-induced cardiovascular effects of the R(+) enantiomer are largely 'masked' by the potent anti-hypertensive effects of the S(−) enantiomer. Furthermore, the amount of racemate which may safely be administered is limited by the hypotensive activity of the S(−) enantiomer which, in excess of about 0.5 mg/kg, can give rise to adverse effects such as a marked and sustained fall in blood pressure and reduced coronary blood flow. The R(+) enantiomer, on the other hand, is expected to provide beneficial cardiovascular effects at concentrations far exceeding those at which the S(−) enantiomer begins to produce unwanted effects. Thus using the racemate of amlodipine places an artificial limit on the amount of R(+) enantiomer which may be administered and deprives the patient of the full cardiovascular benefits of said enantiomer.

One problem which the present invention seeks to address is to provide amlodipine compositions comprising sufficient S(−) enantiomer to achieve the desired anti-hypertensive and anti-anginal effects while also comprising sufficient R(+) enantiomer to maximise the beneficial NO-induced cardiovascular effects of the latter. That is, to improve blood flow to vital organs such as heart, kidney and brain by vasodilation and inhibition of platelet aggregation without affecting normal haemodynamics.

Further benefits likely to be associated with such compositions include improved endothelial function, reduced free radical damage, reduced atheroma and plaque lability and a change in the arterio-venous balance. These, in turn, are likely to have significant 'end organ' benefits, for example, reductions in the rate of acute myocardial infarctions and revascularisation associated with coronary heart disease, chronic renal failure, congestive heart failure and angina.

The ability of the R(+) enantiomer to release vascular NO was studied by (a) measuring nitrite production in canine coronary microvessels, epicardial coronary artery and aorta; and (b) measuring cardiac oxygen consumption in canine myocardium in vitro in the presence of increasing concentrations of the enantiomer using the methods described in *Circulation* 97 576 (1998), Zhang and Hintze.

The R(+) enantiomer gave rise to (a) a concentration-dependent increase in nitrite production up to about 65 pmol/mg at an enantiomer concentration of $10^{-9}$M; and (b) a concentration-dependent reduction in oxygen consumption (down about 30% at an enantiomer concentration of $10^{-5}$M);

both effects were wholly or partly blocked by the NO synthase inhibitor, L-NAME.

In an identical study, the S(−) enantiomer gave no evidence of nitrite production and, while a reduction in oxygen consumption was observed, it was not blocked by L-NAME.

As indicated, maximum NO release as measured by nitrite production was observed at a free concentration of R(+) enantiomer of $10^{-9}$M or 0.4 ng/ml; this figure corresponds to a plasma protein-bound concentration of about 30 ng/ml, that is, some 5× the optimum plasma concentration for the S(−) enantiomer (*Amer J Cardiol* 73 A10–A17 (1994), D N Abernethy et al).

It follows that amlodipine racemate administered for optimum anti-hypertensive effect of the S(−) enantiomer fails to provide sufficient R(+) enantiomer for optimum NO release.

In a further series of experiments based on the known ability of NO to regulate myocardial glucose uptake (*Circ Res* 86 270 (2000), H Tada et al), the ability of the R(+) enantiomer to release vascular NO under hypoxic conditions was studied by measuring (a) the reduction in myocardial glucose uptake (MGU); and (b) the increase in the time to cessation of beating (TCB) of hypoxic Langendorff mouse hearts perfused with a $10^{-7}$M solution of the enantiomer.

The R(+) enantiomer produced (a) a reduction in myocardial glucose uptake of from 0.57 μg/min.mg to 0.27 μg/min.mg, a reduction of over 50%; and (b) an increase in the time to cessation of beating of from 9 minutes to about 33 minutes.

The MGU compares favourably with that of a normoxic heart (0.36 μg/min.mg) and indicates that the R(+) enantiomer goes some way towards protecting the hypoxic heart through modulation of myocardial glucose uptake. This was reflected by an increase in TCB of from 9 minutes to about 33 minutes, a three-fold increase in survival time.

It follows that the dose of amlodipine racemate administered for optimum anti-hypertensive effect of the S(−) enantiomer limits the amount of R(+) enantiomer available for additional protection of the heart from hypoxic damage.

According to the present invention, therefore, there are provided compositions of amlodipine wherein the amount of S(−) enantiomer present is in the range 1.25 mg to 5 mg and the ratio of R(+) enantiomer: S(−) enantiomer exceeds the 1:1 ratio found in the racemate. In order to achieve the desired combination of anti-hypertensive and NO-induced cardiovascular effects, the compositions of the invention typically contain a ratio of R(+) enantiomer: S(−) enantiomer in the range 2:1 to 8:1, ideally about 5:1.

It is also within the scope of the present invention that said compositions may exclusively comprise the R(+) enantiomer when only those cardiovascular effects associated with elevated levels of vascular NO are required, for example, in the treatment of endothelial dysfunction arising from ischaemia and reperfusion of the heart.

It may also be useful to combine the R(+) enantiomer with a cardiovascular drug of alternative mechanism, for example, an ACE inhibitor, such as ramaprilat or quinapril, to provide an additive or synergistic effect. In this connection, it has been reported that amlodipine racemate and the ACE inhibitor ramaprilat appear to be synergistic in enhancing NO production in canine coronary microvessels (*J Cardiovasc Pharmacol* 35 195–202 (2000), Zhang et al) and in regulating myocardial oxygen consumption (*Am J Cardiol* 83 92H–98H (1999), Mital et al). Insofar as the amlodipine is concerned, both effects are presumably being manifested through the R(+) enantiomer.

A similar synergy in NO effect might be expected for the R(+) enantiomer of amlodipine in combination with a PDE5 inhibitor which combination is likely to potentiate the responses to released NO. A particularly preferred PDE5 inhibitor for use in such a combination might be sildenafil.

The R(+) and S(−) enantiomers used in preparing the compositions of the invention may be prepared by chiral synthesis from a suitable optically pure precursor or obtained from amlodipine racemate by any conventional technique, for example, by chromatographic resolution using a 'chiral' column or by the preparation of diastereoisomers, separation thereof and regeneration of the desired enantiomer.

Specifically, diastereoisomers may be obtained by reaction of the racemate with a suitable optically active acid or base. The diasteroisomers are then separated, for example, by chromatography or fractional crystallization, and the desired enantiomer regenerated by treatment with an appropriate base or acid. The other enantiomer may be obtained from the racemate in a similar manner or worked up from the liquors of the first separation.

The enantiomers used in the preparation of the compositions of the invention are conveniently prepared from the free base of the racemate by means of tartrate diastereoisomers using the methodology described in U.S. Pat. No. 5,750,707.

Each of the resulting enantiomers may be used in the form of its free base or converted to a suitable salt using conventional techniques, for example, by treatment with an appropriate acid. Preferred salts for the purpose of preparing the compositions of the invention include the acetate, besylate, citrate, L-lactate, maleate, malonate, mesylate, phosphate, succinate, D-tartrate and L-tartrate (hemi- or full where relevant).

The enriched enantiomer mixtures of the present invention may be prepared by (i) combining appropriate amounts of the two enantiomers, (ii) adding an appropriate amount of 'excess' R(+) enantiomer to amlodipine racemate, or (iii) preparing 'mixed' crystals each containing the required ratio of R(+) and S(−) enantiomers. When preparing enriched mixtures in accordance with these methods, it is within the scope of the invention to combine two free bases, a free base and a salt, or two salts. Furthermore, when combining two salts, the salt of one enantiomer may be combined with the enantiomer or racemate of the same or a different salt.

Compositions according to the invention may be administered alone, but will generally be administered in admixture with a suitable pharmaceutical excipient, diluent, or carrier selected with regard to the intended route of administration and in accordance with standard pharmaceutical practice. For example, the compositions of the invention may be administered orally, buccally, or sublingually in the form of tablets, capsules, ovules, elixirs, solutions, or suspensions, which may contain flavouring or colouring agents, for immediate-, delayed- or controlled-release applications.

Such tablets may contain excipients, such as microcrystalline cellulose, lactose, sodium citrate, calcium carbonate, dibasic calcium phosphate and glycine, disintegrants, such as starch (preferably corn, potato, or tapioca starch), sodium starch glycollate, croscarmellose sodium and certain complex silicates, and granulation binders, such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar, or high molecular weight polyethylene glycols. For aqueous suspensions and/or elixirs, the compositions of the invention may be combined with various sweetening or flavouring agents, colouring matter, or dyes, with emulsifying and/or suspending agents and with diluents, such as water, ethanol, propylene glycol and glycerin, and combinations thereof.

The compositions of the invention may also be administered parenterally, for example, intravenously, intraarterially, intraperitoneally, intrathecally, intraventricularly, intrasternally, intracranially, intramuscularly, or subcutaneously, or they may be administered by infusion techniques. They are best used in the form of a sterile aqueous solution which may contain other substances, for example, enough salts or glucose to make the solution isotonic with blood. If necessary, the aqueous solutions should be suitably buffered, preferably to a pH of from 3 to 9. The preparation of suitable parenteral formulations under sterile conditions is readily accomplished by standard pharmaceutical techniques well-known to those skilled in the art. For oral and parenteral administration to human patients, the daily dosage level of the composition of the invention will usually be from 2.5 mg to 55 mg in single or divided doses.

Thus tablets or capsules of the composition of the invention may contain from 2.5 mg to 55 mg of active material and may be administered singly or two or more at a time as appropriate. The physician will determine the actual dosage which will be most suitable for any individual patient and it will vary with the age, weight and response of the particular patient. The above dosages are exemplary of the average case. There can, of course, be individual instances where higher or lower dosage ranges are merited and such are also within the scope of this invention.

The compositions of the invention may also be administered intranasally or by inhalation and are conveniently delivered in the form of a dry powder inhaler or an aerosol spray presentation from a pressurised container, pump, spray, or nebuliser with the use of a suitable propellant, e.g. dichlorodifluoromethane, trichlorofluoromethane, dichlorotetrafluoroethane, a hydrofluoroalkane, such as 1,1,1,2-tetrafluoroethane (HFA 134A®) or 1,1,1,2,3,3,3-heptafluoropropane (HFA 227EA®), carbon dioxide, or other suitable gas. In the case of a pressurised aerosol, the dosage unit may be determined by providing a valve to deliver a metered amount. The pressurised container, pump, spray, or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a composition of the invention and a suitable powder base, such as lactose or starch.

Aerosol or dry powder formulations are preferably arranged so that each metered dose or 'puff' contains from 2 mg to 10 mg of the composition for delivery to the patient. The overall daily dose with an aerosol will be in the range of from 2.5 mg to 55 mg which may be administered in a single dose or, more usually, in divided doses throughout the day.

Alternatively, the compositions of the invention may be administered in the form of a suppository or pessary, or they may be applied topically in the form of a lotion, solution, cream, ointment, or dusting powder. The compositions may also be administered transdermally, for example, by the use of a skin patch. They may also be administered by the ocular route, particularly for treatment of the eye.

For ophthalmic use, the compositions of the invention may be formulated as micronised suspensions in isotonic, pH-adjusted, sterile saline, or, preferably, as solutions in isotonic, pH-adjusted, sterile saline, optionally in combination with a preservative, such as a benzylalkonium chloride. Alternatively, they may be formulated in an ointment, such as petrolatum.

For topical application to the skin, the composition of the invention may be formulated as a suitable ointment containing the active material suspended or dissolved in, for example, a mixture comprising one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture comprising one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Finally, the compositions of the invention may be administered via intracavernosal injection.

EXAMPLES

The preparation of an enriched enantiomer mixture in accordance with the present invention and pharmaceutical compositions thereof is illustrated by the following examples:

Example 1

Preparation of R(+) Amlodipine Salts from Racemic Amlodipine Besylate (1) Preparation of Racemic Amlodipine Free Base To a slight suspension of racemic amlodipine besylate (100.37 g, 0.177 mol) [prepared by the method described in European Patent No. 0244944] in methylene chloride (250 mL, 2.5 mL/g) and water (250 mL, 2.5 mL/g) was added 11 M sodium hydroxide (24 mL) to achieve pH 13–14. The mixture was stirred for ten minutes during which time it became a solution. The layers were separated and the organic layer washed with water (1×250 mL) and gravity filtered through a magnesium sulphate (25 g) bed. The magnesium sulphate was washed with methylene chloride (40 mL) and to the combined filtrates was added dimethyl sulphoxide (360 mL). The methylene chloride was removed on a rotary evaporator (45 minutes on a water aspirator followed by 15 minutes under high vacuum).

(2) Preparation and Separation of R(+) Amlodipine Tartrate Diastereoisomer

To the dimethyl sulphoxide solution of racemic amlodipine free base obtained in Step (1) was added a solution of L-tartaric acid (6.62 g, 0.044 mol, 0.25 equiv) in dimethyl sulphoxide (360 mL). The solution was stirred at ambient temperature for six hours and the resulting solid collected by suction filtration and washed with acetone (200 mL). (Note: it is important that the dimethyl sulphoxide be completely removed from the solid before the solid is washed with acetone.) The solid was dried in vacuo at 50° C. overnight to give (R)-amlodipine-hemi-L-tartrate-DMSO-solvate (68.25 g) as a pale yellow, tacky solid. The filtrate was set aside and may be used in the isolation of (S)-amlodipine free base.

(3) Preparation of R(+) Amlodipine Free Base

To a solution of the (R)-amlodipine-hemi-L-tartrate-DMSO-solvate (68.25 g) obtained in Step (2) in methylene chloride (345 mL, 5 mL/g) was added a solution of 50% sodium hydroxide (73 mL) in water (72 mL). The solution was stirred at ambient temperature for 40 minutes. The layers were separated and the organic layer extracted with water (1×150 mL) and gravity filtered through a magnesium sulphate (25 g) bed. The magnesium sulphate was washed with methylene chloride (40 mL) and the methylene chloride removed on a rotary evaporator using a water aspirator.

Heptane was added to the evaporation flask as the volume allowed. Eventually, all of the methylene chloride was removed and 600 mL of heptane was added to the flask. The resulting solid was collected by suction filtration, washed with heptane and dried in vacuo at 50° C. overnight to give (R)-amlodipine free base (19.4 g, 53.4% yield) as an off-white solid.

| | |
|---|---|
| Chemical purity by HPLC: | 99.95% |
| Chiral purity by HPLC: | 98.88% |

(4) Preparation of R(+) Salts
  (a) Succinate
  To a solution of the (R)-amlodipine free base (1.0 g, 2.45 mmol) obtained in Step (3) in ethanol (15 mL) was added succinic acid (0.29 g, 2.45 mmol) in ethanol (8 mL). The mixture was allowed to stand at ambient t temperature overnight. The resulting solid was collected by suction filtration, rinsed with cold ethanol and dried in vacuo at 40° C. overnight. An additional 6 hours in vacuo at 60° C. gave the (R)-amlodipine succinate (1.11 g, 86.0% yield) as a white solid.
  (b) Mesylate
  (R)-Amlodipine free base (1.0 g, 2.45 mmol) obtained in Step (3) was dissolved in isopropyl alcohol (23 mL) after fifteen minutes stirring at ambient temperature. Methanesulphonic acid (0.24 g, 2.45 mmol) in isopropyl alcohol (2 mL) was added and the solution stirred at ambient temperature for 3 hours. After cooling in the refrigerator overnight, a small amount of solid had formed which amount slightly increased after a further night in the freezer. The solid was collected by suction filtration, rinsed with cold isopropyl alcohol and dried in vacuo at 40° C. overnight. Drying in vacuo at 80° C. overnight gave the (R)-amlodipine mesylate (1.08 g, 87.4% yield) as a beige solid.

Example 2

Preparation of S(−) Amlodipine Salts from Racemic Amlodipine Besylate

S(−) amlodipine succinate and S(−) amlodipine mesylate may be prepared in analogous fashion using, for example, D-tartaric acid rather than L-tartaric acid in Step (2) to prepare and isolate the corresponding diastereoisomer. Alternatively, the L-tartaric disastereoisomer may be worked up from the liquors left after isolation of the R(+) diastereoisomer.

Example 3

Optional Preparations of Enriched Enantiomer Mixture (1) To 0.5 mole of R(+) enantiomer free base or a salt thereof prepared by a method in accordance with Example 1 was added 0.1 mole of S(−) enantiomer free base or a salt thereof prepared by a method in accordance with Example 2 and the resulting mixture homogenised.
(2) To 0.2 mole of racemic amlodipine besylate was added 0.4 mole of R(+) enantiomer free base or a salt thereof prepared by a method in accordance with Example 1 and the resulting mixture homogenised.
(3) A solution comprising 0.5 mole of R(+) enantiomer free base or a salt thereof prepared by a method in accordance with Example 1 and 0.1 mole of S(−) enantiomer free base or a salt thereof prepared by a method in accordance with Example 2 was allowed to crystallise and the resulting crystals filtered off.

Example 4

Suitable Formulations

| Tablets | |
|---|---|
| | mg/tablet |
| Active ingredient | 24.24 |
| Microcrystalline cellulose Ph Eur | 50.00 |
| Lactose Ph Eur | 121.76 |
| Croscarmellose sodium NF | 2.00 |
| Magnesium stearate Ph Eur | 2.00 |

The active ingredient is sieved and blended with the other components. The resultant mix is compressed into tablets using a rotary tablet press (Manesty Betapress) fitted with 6 mm normal concave punches. The resultant tablets may be film-coated with an appropriate film-coating material.

| Capsules | |
|---|---|
| | mg/capsule |
| Active ingredient | 18.18 |
| Lactose Ph Eur | 208.89 |
| Maize starch Ph Eur | 69.63 |
| Colloidal anhydrous silica Ph Eur | 0.30 |
| Magnesium stearate Ph Eur | 3.00 |
| Fill weight | 300.00 |

The active ingredient is sieved and blended with the other components. The mix is filled into Size No. 2 hard gelatin capsules using suitable machinery. Other doses may be prepared by altering the fill weight and, if necessary, changing the capsule size to suit.

What is claimed is:

1. A pharmaceutical composition comprising an NO-releasing amount of the R(+) enantiomer of amlodipine or of a pharmaceutically acceptable salt thereof, an antihypertensive amount of the S(−) enantiomer of amlodipine or of a pharmaceutically acceptable salt thereof and a suitable excipient, diluent, or carrier, wherein the enantiomers are present in a ratio by weight (based on free base) of R(+) enantiomer: S(−) enantiomer of 2:1 to 8:1.

2. A pharmaceutical composition according to claim 1 wherein said ratio is approximately 5:1.

3. A pharmaceutical composition according to claim 1 which comprises a mixture of single crystals of the R(+) enantiomer or pharmaceutically acceptable salt thereof and single crystals of the S(−) enantiomer or pharmaceutically acceptable salt thereof.

4. A pharmaceutical composition according to claim 3 wherein both enantiomers are in the form of pharmaceutically acceptable salts.

5. A pharmaceutical composition according to claim 4 wherein the salts of both enantiomers have the same counter ion.

6. A pharmaceutical composition according to claim 1 which comprises single crystals of the R(+) enantiomer or pharmaceutically acceptable salt thereof and mixed crystals containing both the R(+) enantiomer and the S(−) enantiomer or pharmaceutically acceptable salts of one or both thereof.

7. A pharmaceutical composition according to claim 6 wherein the mixed crystals are racemic.

8. A pharmaceutical composition according to claim 6 or 7 wherein the R(+) enantiomer is in the form of a pharmaceutically acceptable salt and the enantiomers in the mixed crystals are also in the form of pharmaceutically acceptable salts.

9. A pharmaceutical composition according to claim 6 or 7 wherein the salt of the R(+) enantiomer and the salts of the enantiomers in the mixed crystals have the same counter ion.

10. A pharmaceutical composition according to claim 1 which comprises mixed crystals containing both the R(+) enantiomer or pharmaceutically acceptable salt thereof and the S(−) enantiomer or pharmaceutically acceptable salt thereof.

11. A pharmaceutical composition according to claim 10 wherein both enantiomers are in the form of pharmaceutically acceptable salts.

12. A pharmaceutical composition according to claim 11 wherein the salts of both enantiomers have the same counter ion.

13. A pharmaceutical composition according to claim 5 wherein said counter ion is mesylate or succinate.

14. A pharmaceutical composition according to claim 9 wherein said counter ion is mesylate or succinate.

15. A pharmaceutical composition according to claim 12 wherein said counter ion is mesylate or succinate.

16. A pharmaceutical composition according to claim 1 which is in the form of a tablet or capsule suitable for oral administration.

17. A pharmaceutical composition according to claim 1 which is in liquid dosage form.

18. A pharmaceutical composition according to claim 1 which is in the form of a solution suitable for intravenous (iv) administration.

19. A pharmaceutical composition according to claim 1 for use in the treatment of a condition for which a vascular NO-releasing agent is indicated.

* * * * *